(12) United States Patent
Bublick et al.

(10) Patent No.: US 9,622,902 B1
(45) Date of Patent: Apr. 18, 2017

(54) CUFF AND CUFF/CONDOM COMBINATION FOR ERECTION ASSISTANCE

(71) Applicants: Ronald G Bublick, Virginia Beach, VA (US); Linda L Bublick, Virginia Beach, VA (US)

(72) Inventors: Ronald G Bublick, Virginia Beach, VA (US); Linda L Bublick, Virginia Beach, VA (US)

(73) Assignee: ENCORE PRODUCTS INC, Virginia Beach, VA (US)

( * ) Notice: Subject to any disclaimer, the term of this patent is extended or adjusted under 35 U.S.C. 154(b) by 0 days.

(21) Appl. No.: 15/068,848

(22) Filed: Mar. 14, 2016

(51) Int. Cl.
*A61F 5/00* (2006.01)
*A61F 5/41* (2006.01)

(52) U.S. Cl.
CPC .......... *A61F 5/41* (2013.01); *A61F 2005/411* (2013.01); *A61F 2005/414* (2013.01); *A61F 2005/415* (2013.01)

(58) Field of Classification Search
CPC ........ A61F 5/41; A61F 2005/411; A61F 6/02; A61F 6/04
USPC ............................... 600/38–41; 128/842–844
See application file for complete search history.

(56) References Cited

U.S. PATENT DOCUMENTS

| | | | | |
|---|---|---|---|---|
| 4,893,616 | A * | 1/1990 | Immonen | A61F 5/41 600/39 |
| 5,868,137 | A * | 2/1999 | Brown | A61F 5/41 128/842 |
| 9,295,579 | B1 * | 3/2016 | Bublick | A61F 5/41 |
| 2014/0171734 | A1 * | 6/2014 | Kassman | A61H 19/50 600/38 |

* cited by examiner

*Primary Examiner* — John Lacyk
(74) *Attorney, Agent, or Firm* — Peter J. Van Bergen

(57) ABSTRACT

A device providing erection assistance includes an open-ended and radially elastic tubular cuff adapted to fit over a male penis. The cuff's length is such that it can extend from the base of the penis to as far as the corona thereof. The cuff includes at least one wall region defining a void region along the wall region's length.

39 Claims, 8 Drawing Sheets

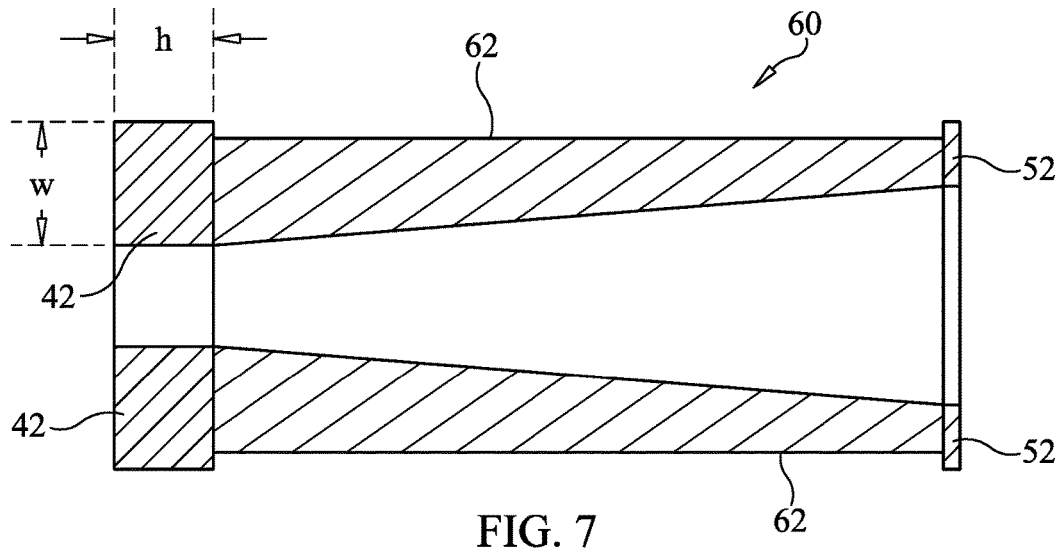
FIG. 7
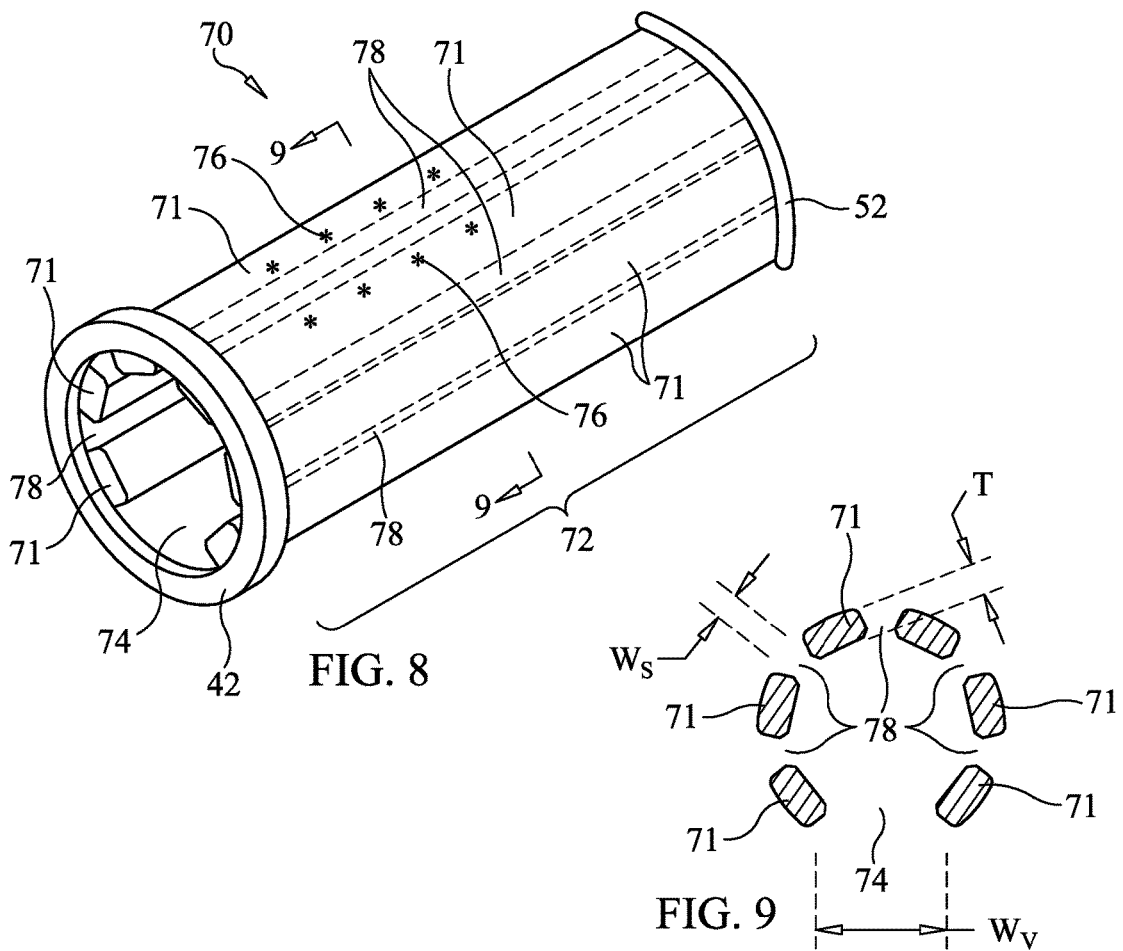
FIG. 8
FIG. 9

CUFF AND CUFF/CONDOM COMBINATION FOR ERECTION ASSISTANCE

CROSS-REFERENCE TO RELATED PATENT APPLICATIONS

This patent application is co-pending with one related patent application entitled "CUFF AND CUFF/CONDOM COMBINATION FOR ERECTION ASSISTANCE", application Ser. No. 14/824,650, filed Aug. 12, 2015.

FIELD OF THE INVENTION

The invention relates generally to non-surgical-based sexual aids, and more particularly to cuffs and cuff/condom combinations that provide erection assistance and/or erection enhancement.

BACKGROUND OF THE INVENTION

Options for males experiencing some degree of erectile dysfunction (or "ED" as it is also known) include worn devices, surgically-implanted devices, external equipment, surgeries, and ingested medications. Surgically-implanted devices, external equipment, and ingested medications are expensive, and can present a variety of post-use health risks and/or potential side effects with ingested medications having potential adverse reactions including fatal events. Worn devices generally avoid the expense and health risks associated with implanted devices and medications. However, existing worn devices are relatively few in number, have little credibility, and have not been effective thereby leaving ED-afflicted males with no solution other than reliance on the more expensive and riskier surgeries, surgically-implanted devices and more expensive ingested medications.

SUMMARY OF THE INVENTION

Accordingly, it is an object of the present invention to provide a device for use by a male to improve his sexual experience.

Another object of the present invention is to provide a simple and effective device that can be worn by a male experiencing some degree of erectile dysfunction in order to provide erection assistance.

Still another object of the present invention is to provide a device that can be used by a male as a non-surgical-based, non-medicinal aid for erectile dysfunction that presents no potential health risks to the male or his partner.

Other objects and advantages of the present invention will become more obvious hereinafter in the specification and drawings.

In accordance with the present invention, a device providing erection assistance includes an open-ended tubular cuff having radial elasticity. The cuff is adapted to fit over a male penis and has a length that allows the cuff to extend from the base of the penis to as far as the corona thereof. The cuff includes at least one wall region defining a void region along the wall region's length. Additional embodiments of the present invention can include the use of one or more elastic rings coupled to the wall region(s), indicia on the cuff in diametric opposition to the void region, an enhanced ring coupled to the wall region(s), and/or a sleeve coupled to the cuff such that the combination of the cuff and sleeve define a condom.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 7 is an axial cross-sectional view of a cuff whose tubular wall region's thickness varies as a function of axial location in accordance with another embodiment of the present invention;

FIG. 8 is a perspective view of a cuff that includes multiple, spaced-apart wall regions or strips in accordance with another embodiment of the present invention;

FIG. 9 is a cross-sectional view taken along line 9-9 in FIG. 8;

DETAILED DESCRIPTION OF THE INVENTION

Figure 1:
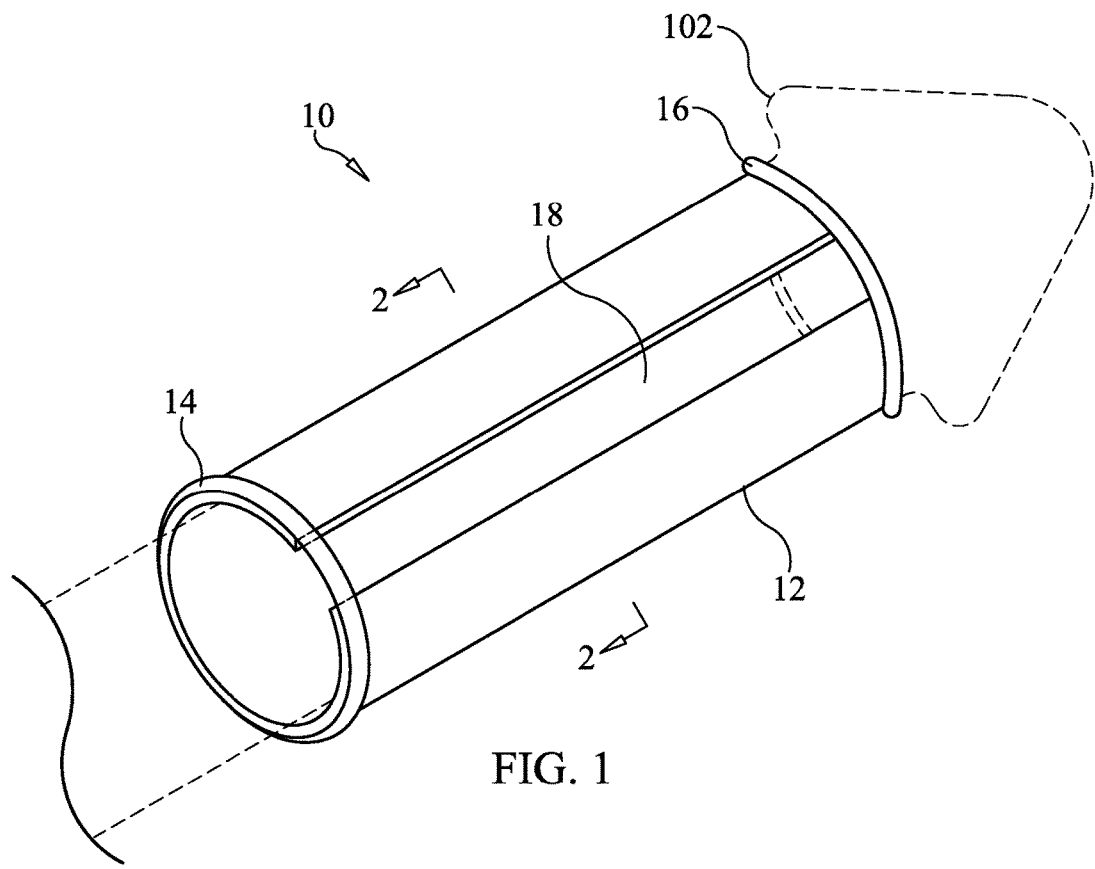
FIG. 1 is a perspective view of a cuff that can be worn by a male in accordance with an embodiment of the present invention.

Referring now to the drawings, simultaneous reference will be made to FIGS. 1-3 where an embodiment of a cuff for use as a non-surgical-based and non-medicinal device that provides erection assistance for a male is shown and is referenced generally by numeral 10. Cuff 10 can be used by a male experiencing some or any degree of erectile dysfunction (or "ED"), or by a male seeking a firmer and/or longer-lasting erection. Cuff 10 is generally an open-ended tube having a tubular body 12 terminating at axial ends thereof in bands or rings 14 and 16. Rings 14 and 16 can be similar to the rolled ring formed at the opening of conventional condoms or can be constructed/configured in accordance with any of the other rings described later herein. Rings 14 and 16 are coupled to tubular body 12.

In general, cuff 10 is placed on/over a flaccid, partially erect, or erect male penis to thereby provide erection assistance to the wearer. As used herein, the term "erection assistance" means that cuff 10 in combination with a flaccid, partially erect, or erect penis provides firmness that helps support sexual intercourse. In terms of length, cuff 10 is sized to fit just behind the corona 102 (i.e., the ridge around the base of the head of the penis) of a penis (shown in dashed lines), and extend to the base of the penis. Materials used for cuff 10 can include, but are not limited to, elastic materials used in the manufacture of condoms to include latex/natural rubber, all forms of synthetic rubber, polyester, polyethylene, plastics, lambskin, and combinations thereof. Cuff 10 can be constructed to stretch (e.g., using materials that inherently stretch) outward in the radial direction such that it applies inward radial pressure when used. That is, cuff 10 has radial elasticity that can be provided just by tubular body 12 or by a combination of tubular body 12 and rings 14/16. Cuff 10 could be made in one size, several general or specific sizes, or could be specially sized such that its diameter is adapted for a specific user.

Tubular body 12 is a monolithic solid or hollow-wall, open-ended, split-ring cylinder. In the illustrated embodiment, tubular body 12 is a solid-wall structure that is substantially tubular except for a gap or void 18 defined all along the length of tubular body 12. Tubular body 12 can be made using elastic materials typically used in the manufacture of condoms such that tubular body 12 has radial elasticity. Tubular body 12 is not a thin-wall and flaccid structure as is the case with conventional condoms (i.e., wall thicknesses in the range of approximately 0.03-0.09 millimeters). Rather and for example, when tubular body 12 is made using a condom-type of latex or other condom material, the thickness T of tubular body 12 can be in the range of approximately 0.1 inches to approximately 0.5 inches. In the illustrated embodiment, thickness T is constant all along the length of tubular body 12. However, the thickness of tubular body 12 can vary along the length thereof and/or can be tapered at the axial ends thereof as will be explained later herein.

In use, the gap or void 18 defined by tubular body 12 is to be aligned with the wearer's urethral tube that runs along the length of the underside of the penis. When aligned with the wearer's urethral tube, void 18 defines a region of cuff 10 along which little to no radial pressure will be applied to the wearer's penis. The width $W_V$ of void 18 can be in the range of approximately 0.125 inches to approximately 0.75 inches with the larger widths providing a spacing that accommodates slight misalignment and anatomical differences between users.

To provide alignment guidance, tubular body 12 can have visual and/or tactile indicia to assist with alignment of cuff 10. For example and as shown in the 180° rotated view of cuff 10 illustrated in FIG. 3, the alignment indicia can include verbiage 20 (e.g., "THIS SIDE UP" as shown) indicating the top of cuff 10 (as viewed when worn). Verbiage 20 is located in diametric opposition to void 18 to facilitate alignment of void 18 with the wearer's urethral tube. Verbiage 20 can be printed letters, and/or can be formed by raised letters, shapes, etc., to provide a tactile indicator for proper alignment. Verbiage 20 (and/or tactile indicia) can be provided on the outer surface of tubular body 12, and can be of a color that is the same or different from the color used for tubular body 12. The firmness of cuff 10 helps provide erection assistance to a flaccid or partially erect penis (and can also help even an erect penis remain that way for a longer period of time), while void 18 provides for reduced impediment of seminal or other body fluids flow through the wearer's urethral tube.

As mentioned above, tubular body 12 terminates at its opposing axial ends in bands or rings 14 and 16. Each of rings 14 and 16 is generally elastic and sized to snugly fit on a penis to retain the shape of tubular body 12 and to hold/retain cuff 10 in place without slippage. Rings 14 and 16 can be made from the same or different materials and/or colors as tubular body 12 without departing from the scope of the present invention. Rings 14 and 16 can be integrally formed with or sealed to tubular body 12. Each of rings 14 and 16 could be formed by a rolled amount of the material used for tubular body 12 and be similar to the rolled ring end of a conventional condom. Once placed on a flaccid, partially erect, or erect penis, cuff 10 provides axial rigidity forces to the penis such that the combination of the penis and cuff 10 presents a structure suitable for sexual intercourse. As will be explained further below, tubular body 12 on its own and/or tubular body 12 in combination with rings 14 and 16 also provide inward radial pressure in a way that promotes, helps attain, and/or maintains an erection. Ring 14 and/or ring 16 (and/or tubular body 12) could also have vibrating device(s)/element(s) coupled thereto without departing from the scope of the present invention. One or more additional rings could be provided at any position(s) along tubular body 12 where such additional ring(s) can be integrally formed with tubular body 12, or manually placed thereon during or after the manufacturing process, without departing from the scope of the present invention.

Figure 2:
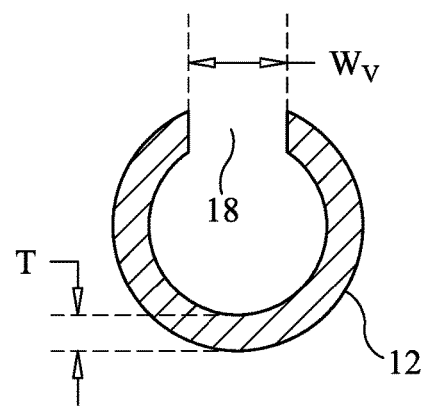
FIG. 2 is a cross-sectional view taken along line 2-2 in FIG. 1.
Figure 3:
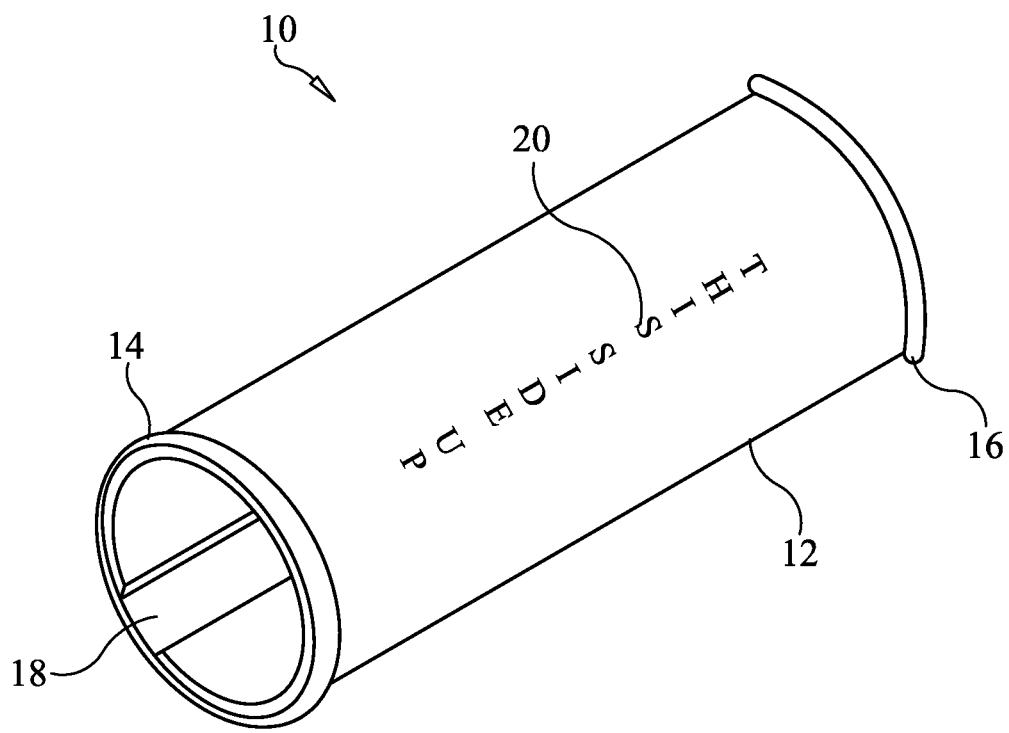
FIG. 3 is a perspective view of the cuff in FIG. 1 rotated 180° about its longitudinal axis.
Figure 4:
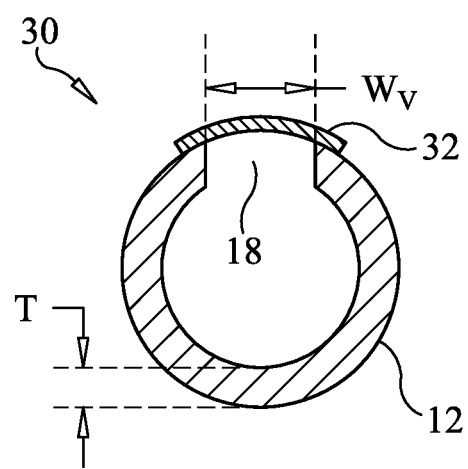
FIG. 4 is a cross-sectional view of a cuff with a covered void in accordance with another embodiment of the present invention.

Void 18 in tubular body 12 could remain uncovered (as shown in FIGS. 1-3) or could be covered as illustrated in FIG. 4 without departing from the scope of the present invention. Referring to FIG. 4, a cuff 30 includes all elements and features of the above-described cuff 10, and further includes material 32 coupled to tubular body 12 on its outside surface (as shown). Material 32 can also be coupled to the inside surface of tubular body 12, or both the outside and inside surfaces of tubular body 12, without departing from the scope of the present invention. Material 32 spans void 18 and can be a thin and flaccid material whose thickness can be generally equivalent to that of a conventional condom.

Figure 5:
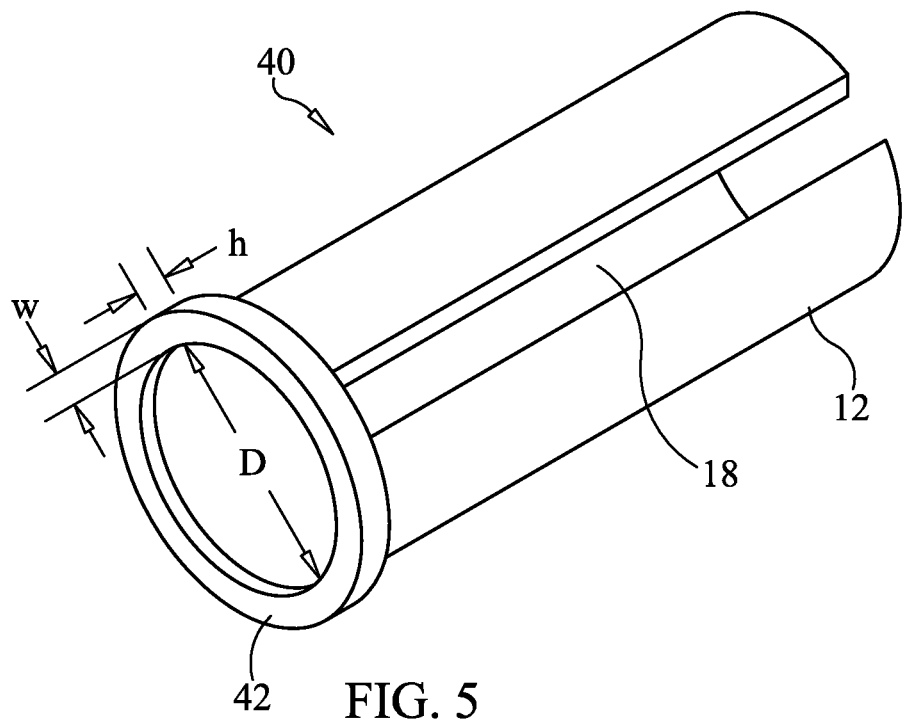
FIG. 5 is a perspective view of a cuff having a ring in accordance with another embodiment of the present invention.

Without departing from the scope of the present invention, a variety of structural realizations are possible for a cuff that applies inward radial pressure forces to a penis. For example, FIG. 5 illustrates another cuff embodiment of the present invention that is referenced generally by numeral 40. In this embodiment, cuff 40 is similar to cuff 10 described above, but replaces ring 14 and/or 16 with a solid, semi-solid (e.g., includes made from a rolled material), or hollow-wall ring 42 made from a material used in the manufacture of condoms. The edges of ring 42 can be angled/beveled or rounded for user comfort. In general, the height ("h") and width ("w") dimensions of ring 42 (i.e., height h being in the axial dimension of cuff 10 and width w being in the radial dimension of cuff 10) are significantly greater than that of the rolled material at the open end of a conventional condom. For example, when using a condom-type of latex or other condom material for ring 42, the height h for ring 42 is in the range of approximately 0.1875 inches to approximately 5 inches (or more for some applications) and the width w is in the range of approximately 0.1875 inches to approximately 0.5 inches (or more for some applications). The inner diameter "D" of ring 42 should form a snug fit with the base and/or shaft of a penis. In this way, ring 42 will still be able to stretch elastically to fit onto a penis, but its above-defined height/width dimensions will also apply a greater amount of inward radial pressure to a penis as compared to a conventional condom's rolled ring.

It is to be understood that ring 42 could also be positioned at other axial locations along tubular body 12 and positioned on or coupled/sealed thereto, or that more than one ring 42 or other types of rings described herein could be positioned at axial locations along tubular body 12 and positioned on or coupled/sealed thereto, without departing from the scope of the present invention. Still further, one or more additional rings can be positioned on or coupled to tubular body 12 to help retain its shape and/or create additional radial-inward pressure on a penis during use in order to help retain blood in the penis thereby aiding penile firmness and a user's ability to engage in more satisfying sexual intercourse.

Figure 6:
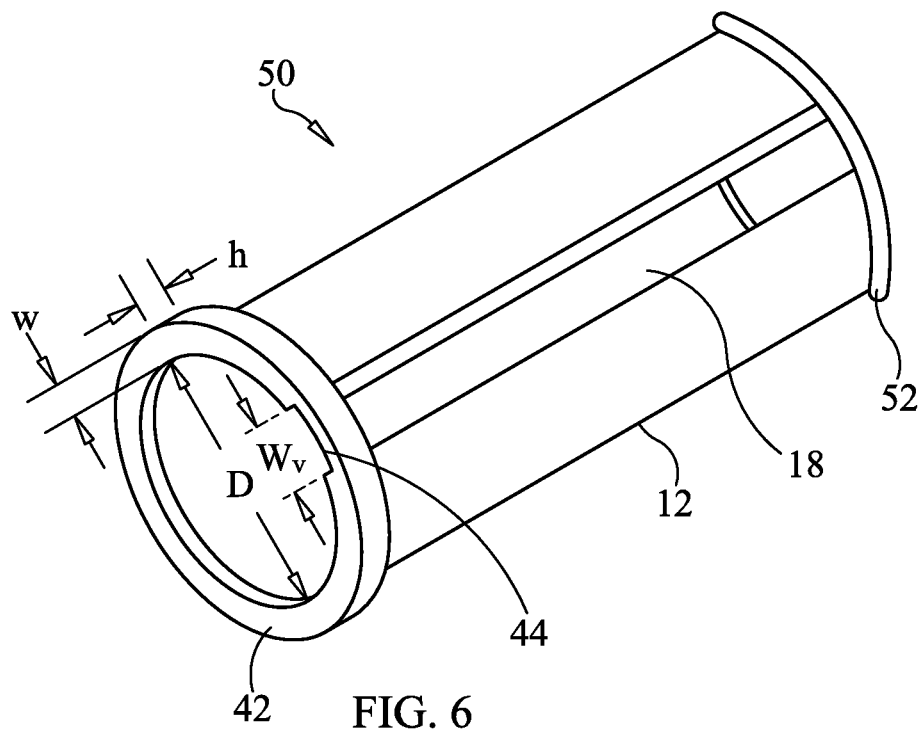
FIG. 6 is a perspective view of a cuff having a notched ring and a retention ring in accordance with another embodiment of the present invention.

FIG. 6 illustrates another embodiment of the present invention where a cuff 50 includes all of the elements and features of the above-described cuff 40, and further includes a ring 42 having a notch 44 formed therein and a retention ring 52 at the longitudinal end of tubular body 12 that opposes the end having ring 42 coupled thereto. Ring 52 is similar to the above-described ring 16 and can be made from the same material as the rest of cuff 50 or from other condom materials, and can be coupled/sealed to tubular body 12. As described above, ring 52 can be positioned at different axial locations along tubular body 12 that are spaced apart from base ring 42 without departing from the scope of the present invention. Additional rings similar to ring 52 could also be provided at one or more axial locations along tubular body 12 without departing from the scope of the present invention.

Cuff 50, as well as any of the other cuffs and cuff/condom combinations described herein, can have a notched ring 42. More specifically, ring 42 can have a notch 44 formed therein that faces radially inward from ring 42. Notch 44 can be sized and positioned to be aligned with void 18 to thereby provide the same advantages as void 18 when cuff 50 is worn. Ring 42 can be on the outside of tubular body 12 (as shown) or on the inside of tubular body 12 without departing from the scope of the present invention. Ring 42 with notch 44 can be a monolithic structure or can be an assembled structure (e.g., a split ring having material spanning the split ring's gap with the gap thereby defining the above-described notch as will be described later herein). Still further, it is to be understood that any of the rings described herein can be notched as described herein.

The thickness of tubular body 12 can be the same along its length or could be varied along its length without departing from the scope of the present invention. For example, FIG. 7 is an axial cross-sectional view of another cuff 60 similar to cuff 50, but having a tubular body 62 whose thickness varies along its length. In the illustrated embodiment, tubular body 62 is thicker at one end (e.g., the end near ring 42) than at its other end (e.g., the end near ring 52). In this way, a user could place the thicker-wall and more rigid portion of tubular body 62 near ring 42 at the base of his penis so that the thinner-wall portion of tubular body 62 is adjacent the penis' corona to maintain comfort and sensitivity. It is to be understood that the scale of varying-thickness tubular body 62 has been exaggerated for purposes of illustration.

The present invention is not limited to the use of a single-wall tubular body. That is, the cuff of the present invention could also use multiple, spaced-apart solid-wall regions or solid strips (as they will be referred to hereinafter) of material. In general, such solid strips take the place of the above-described single-wall tubular body. While each individual strip does not provide a substantial amount of horizontal rigidity, the combination of multiple, spaced-apart solid strips coupled to rings at opposing longitudinal ends of the strips define a multiple-beam structure.

Figure 10:
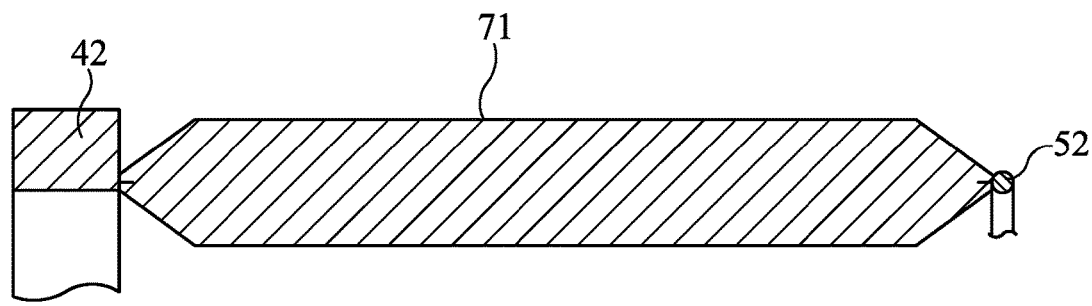
FIG. 10 is a longitudinal cross-section of a single wall region/strip having tapered longitudinal ends in accordance with an embodiment of the present invention.

By way of example, FIGS. 8 and 9 illustrate a cuff 70 having a plurality of axially-extending and spaced-apart strips 71 aligned and distributed in a spaced-apart fashion to define a tubular body 72. Each of strips 71 extends substantially along the length of tubular body 72. Each of strips 71 can be made from the same or different material, e.g., materials used in the manufacture of conventional condoms. Strips 71 can all be the same size. However, different sizes (e.g., length, width, thickness, etc.) of strips 71 could be used to enhance extension/rigidity forces without departing from the scope of the present invention. When using a condom-type of latex or other condom material for strips 71, the thickness T of each strip 71 can be in the range of approximately 0.1 inches to approximately 0.5 inches. The cross-sectional shape of strips 71 can be round, oblong, triangular, square, etc., and is not a limitation of the present invention. In the illustrated example, each of strips 71 is generally rectangular with its corners being rounded or chamfered for user comfort. The opposing longitudinal ends of each strip 71 can be tapered (or rounded) for user comfort as illustrated in FIG. 10 where a single strip 71 is illustrated in a longitudinal cross-section thereof with its opposing longitudinal ends coupled/sealed to ring 42 and retention ring 52 as described above.

As with the previous embodiments, a gap or void 74 is defined along tubular body 72 and indicia 76 (i.e., visual and/or tactile indicia) can (optionally) be provided on one or more of strips 71 defining tubular body 72 in diametric (or approximate diametric) opposition to void 74. In the illustrated example, indicia 76 comprises marks placed along longitudinal edges of two adjacent strips 71 where the marked longitudinal edges are in diametric opposition to void 74. Void 74 is analogous in size and function to void 18 described earlier herein. Spaced-apart strips 71 can be provided in an even distribution about the tubular body on both sides of void 74, or in a varied distribution, without departing from the scope of the present invention. In general, the width $W_S$ of each longitudinal space 78 between strips 71 (other than those on either side of void 74) is less than the width $W_V$ of void 74. By way of a non-limiting illustrative example, for strips 71 that are approximately 0.25 inches wide, the width $W_S$ can be approximately 0.125 inches. The width $W_V$ of void 74 can be in the range of approximately 0.125 inches to approximately 0.75 inches.

Figure 11:
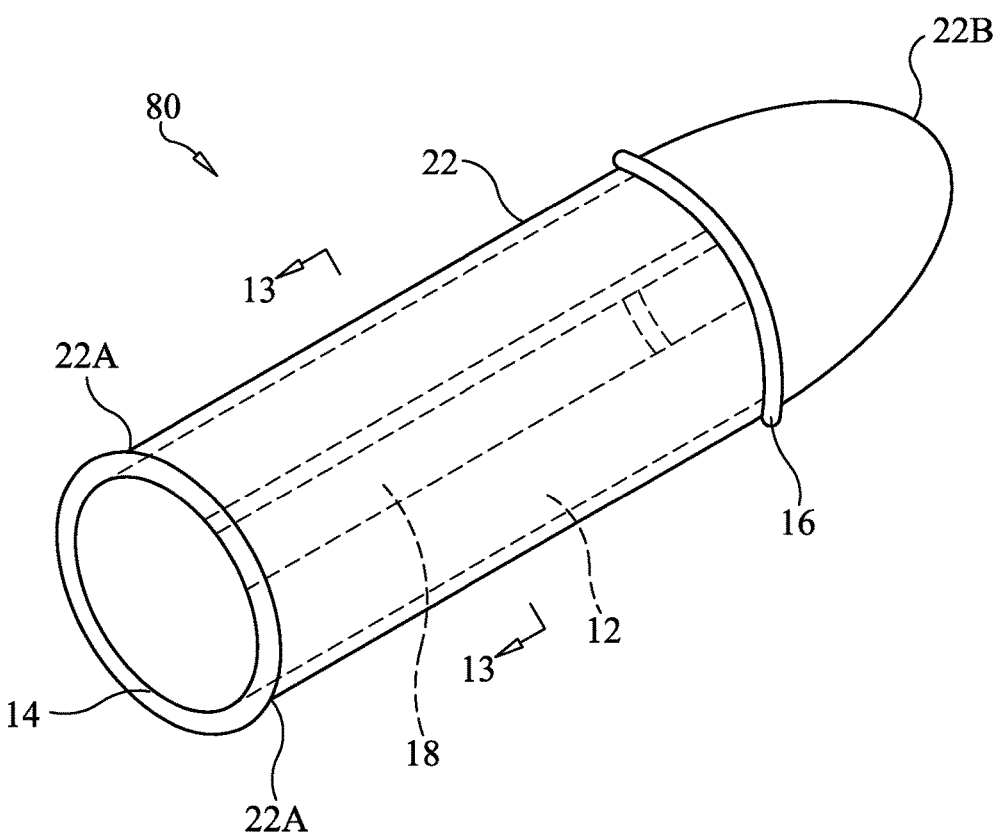
FIG. 11 is a perspective view of a cuff and condom combination in accordance with an embodiment of the present invention.
Figure 12:
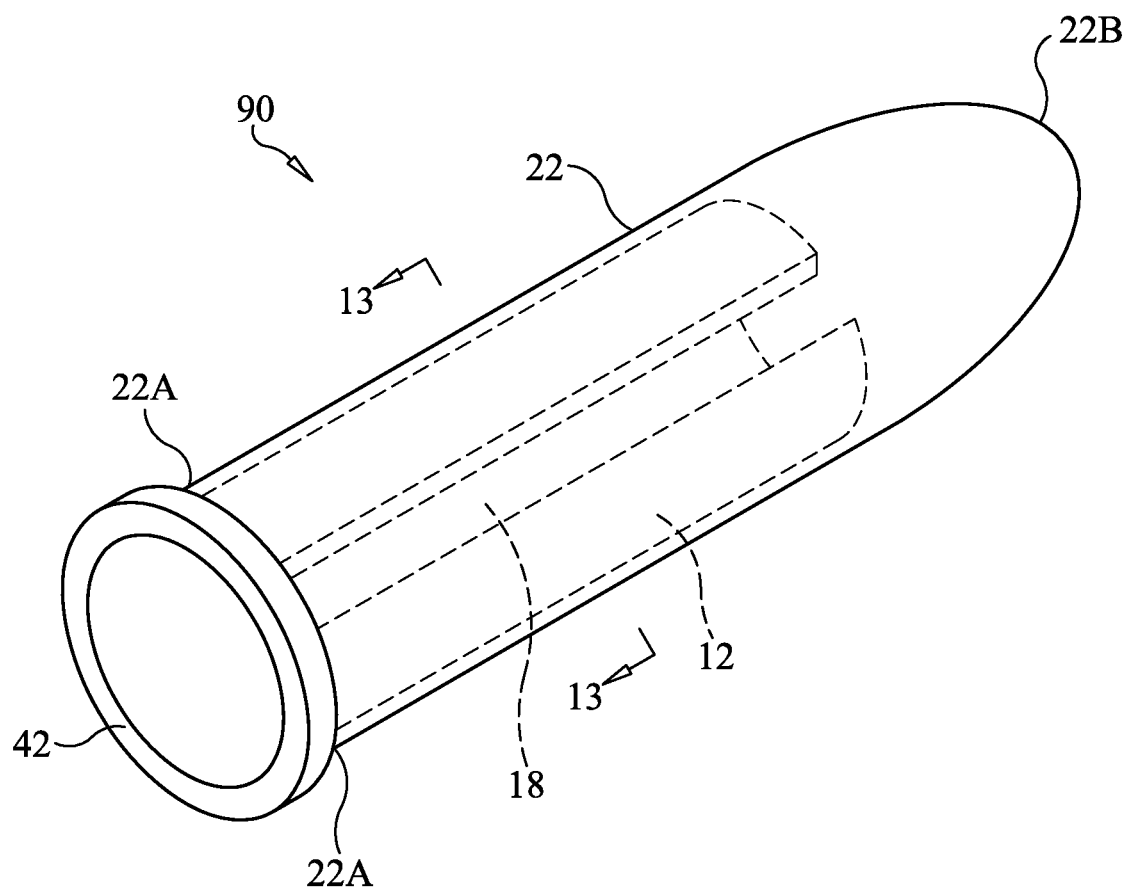
FIG. 12 is a perspective view of a cuff and condom combination in accordance with another embodiment of the present invention.

Any of the above-described cuffs of the present invention can also be incorporated into a condom. For example, each of FIG. 11 and FIG. 12 illustrate a cuff/condom combination referenced generally by numeral 80 and 90, respectively. Cuff/condom 80 is based on the previously-described cuff 10, and cuff/condom 90 is based on the previously-described cuff 40. However, it is to be understood that any of the above-described cuff embodiments (or permutations thereof shown and/or suggested by the instant description) could form the basis of a cuff/condom combination without departing from the scope of the present invention. In each of cuff/condom 80 and 90, a sleeve 22 is coupled/sealed to the respective cuff such that the combination defines a condom. In each case, sleeve 22 is a sleeve of flaccid and elastic material having an open annular end 22A and a closed end or tip 22B. Sleeve 22 is made from a thin, flaccid material having material and dimensional attributes generally similar to those used in the manufacture of conventional condoms.

For example, the thickness of sleeve 22 will generally be in the range of approximately 0.03 millimeters (mm) to approximately 0.09 mm.

Figure 13:
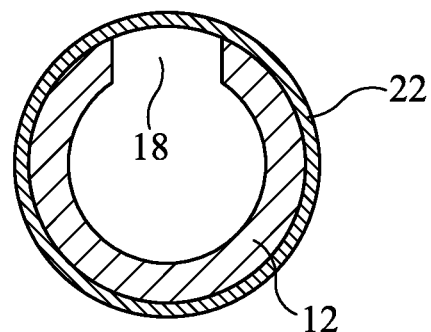
FIG. 13 is a cross-sectional view of the cuff and condom combinations taken along line 13-13 in each of FIGS. 11 and 12.

For cuff/condom 80, annular open end 22A can be coupled to ring 14. Some or all of the portions of sleeve 22 adjacent to tubular body 12 and ring 16 can also be sealed to or integrated therewith. Each of rings 14 and 16 can be located on the inside or outside surface of sleeve 22 without departing from the scope of the present invention. For cuff/condom 90, open annular end 22A can be sealed to or integrated with base ring 42. Some or all of the portions of sleeve 22 adjacent to tubular body 12 can also be sealed to or integrated therewith. Base ring 42 can be located on the inside surface or outside surface of sleeve 22 without departing from the scope of the present invention. For each of the cuff/condom combinations, tip 22B can be configured in a variety of ways without departing from the scope of the present invention. In each of the above-described embodiments, tubular body 12 is on the inside of sleeve 22 as shown in FIG. 13. However, it is to be understood that tubular body 12 could also be on the outside of sleeve 22 without departing from the scope of the present invention. In each of the above-described embodiments, indicia (not shown) can be placed/provided on one or both of sleeve 22 and tubular body 12 in diametric opposition to void 18 as previously described herein.

Inward radial forces applied by the present invention to a penis can be the primary cause of a somewhat firm, firm, or an erect structure defined by a male's penis in combination with one of the present invention's cuff or cuff/condom. In addition, the present invention non-invasively helps the natural erection process by impeding blood flow from the penis as and after a partial or full erection has started or been achieved. The present invention non-invasively assists the holding of blood in a penis to thereby aid in firming a penis and the maintenance of such firmness.

Figure 14:
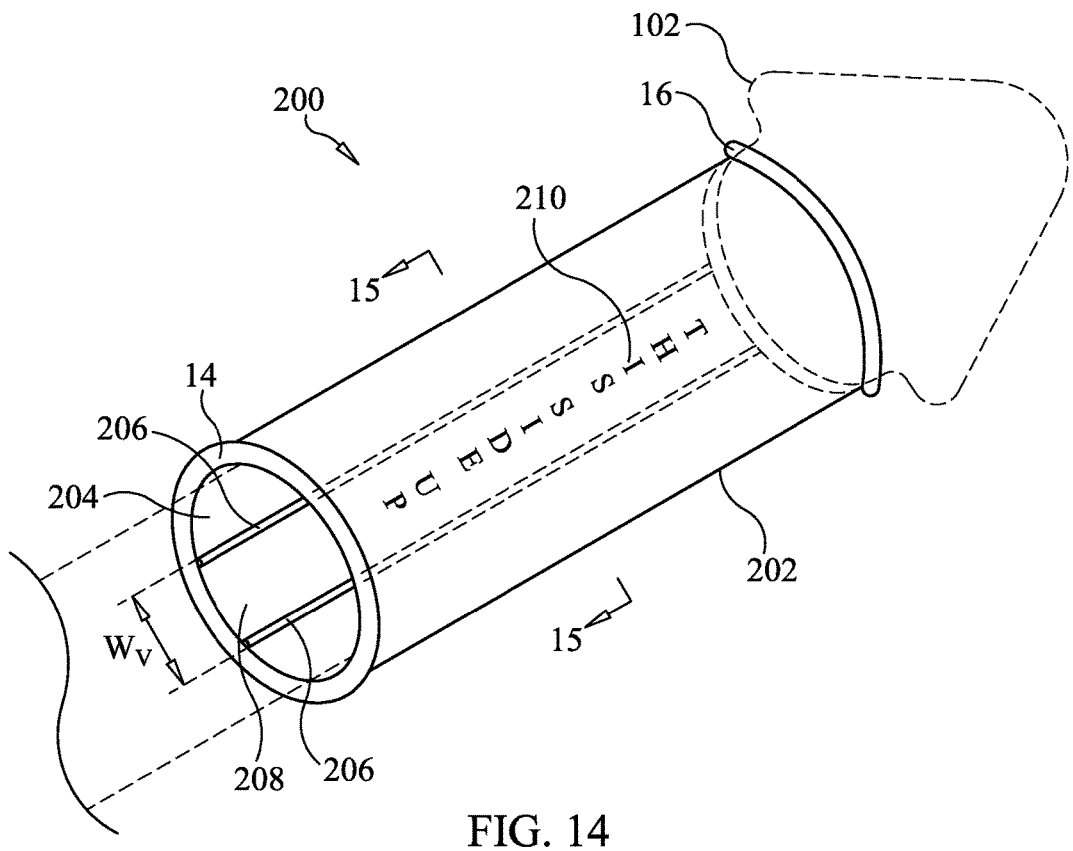
FIG. 14 is a perspective view of a cuff having axially-extending internal ridges defining a urethral tube void region in accordance with another embodiment of the present invention.
Figure 15:
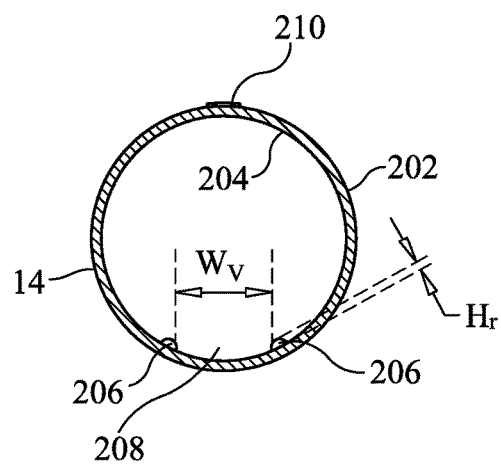
FIG. 15 is a cross-sectional view taken along line 15-15 in FIG. 14.

Another embodiment of the present invention is illustrated in FIGS. 14-15 where a cuff 200 has an open-ended tubular body 202 whose elastic material and wall thickness can be similar to that of a conventional condom. Similar to the various embodiments of the above-described cuffs, cuff 200 is sized to fit just behind the corona 102 of a penis and extend to its base region. The interior surface 204 of body 202 has two axially-extending and spaced-apart ridges 206 coupled thereto or integrated therewith such that ridges 206 protrude radially into body 202 as indicated by radial height "$H_r$". Ridges 206 are spaced apart by a distance $W_V$ to thereby define a void region 208 between the ridges that is analogous the above-described void 18. The distance $W_V$ can range from approximately 0.125 inches to approximately 0.75 inches. Indicia 210 can be provided on body 202 in diametric opposition to void region 208 thereby allowing a user to readily position cuff 200 on a penis such that void region 208 will be aligned with the penis' urethral tube. That is, when cuff 200 is worn with indicia 210 facing up as described earlier herein, ridges 206 will rest against the wearer's penis on both sides of the penis's urethral tube such that the portion of body 202 spanning void region 208 between ridges 206 is offset from the penis and does not apply radial inward pressure to the penis in the area of the urethral tube. Cuff 200 can have ring(s) 14/16 at one end and/or both ends thereof, or could utilize one or more of the above-described enhanced ring 42 (not shown) with or without the notch, without departing from the scope of the present invention.

Figure 16:
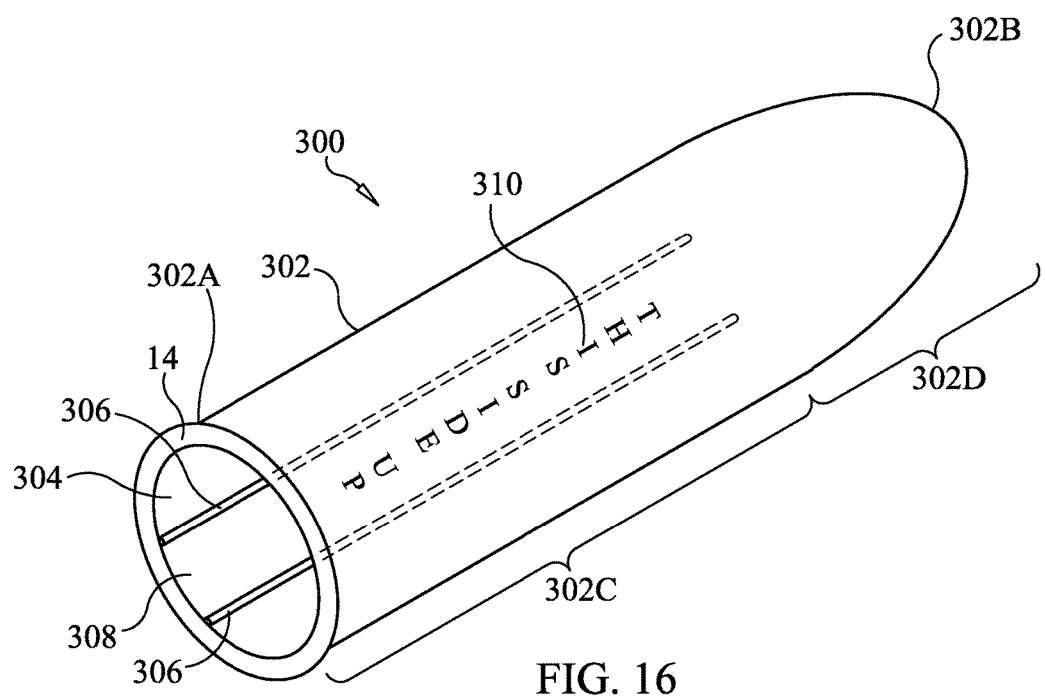
FIG. 16 is a perspective view of the cuff shown in FIG. 14 integrated with a closed-end sleeve to define a condom in accordance with another embodiment of the present invention.

The above-described cuff 200 can have a closed-end sleeve coupled to or integrated with one open end of body 202 such that the combination of cuff and closed-end sleeve define a condom. For example and with reference to FIG. 16, a condom 300 includes the attributes of the above-described cuff 200, but does so using a tubular body 302 that is open on one end 302A and closed at its other end or tip 302B. That is, body 302 essentially consists of a cuff portion 302C (i.e., analogous to cuff 200) coupled to or integrated with a closed-end sleeve portion 302D. Body 302 is similar in material and construction to that of a conventional condom; however, its interior surface 304 has axially-extending ridges 306 from open end 302A to a region of body 302 that will be at or near the corona of a wearer's penis. A region 308 between ridges 306 defines the condom's urethral tube void region having attributes as described previously herein. Indicia 310 can be placed on body 302 in diametric opposition to region 308.

The advantages of the present invention are numerous. The cuff and cuff/condom combination are simple and inexpensive devices that can be used when needed or desired to provide a firmer penis and/or erection assistance. Use of each device requires no surgery or surgical implantation, no medication or supporting equipment, and has no medical side effects or adverse effects. The present invention can provide aid to those with some degree of ED caused by a variety of health issues, including but not limited to, heart diseases, vascular problems, prostate and other cancers, diabetes, as well as health issues caused by medications such as blood thinners or other hundreds of medications including those used for treatment of psychologically-induced sexual problems.

Although the invention has been described relative to specific embodiments thereof, there are numerous variations and modifications that will be readily apparent to those skilled in the art in light of the above teachings. For example, the various rings described herein can be positioned inside of or outside of the various cuffs and cuff/condom combinations without departing from the scope of the present invention. It is therefore to be understood that, within the scope of the appended claims, the invention may be practiced other than as specifically described.

What is claimed as new and desired to be secured by Letters Patent of the United States is:

1. A device providing erection assistance, comprising:
   an open-ended tubular cuff having radial elasticity, said cuff being adapted to fit over a male penis and having a length extending from the base of the penis to as far as the corona of the penis, said cuff including at least one wall region defining a void region along a length of said at least one wall region; and
   a sleeve of flaccid and elastic material having an annular open end and a closed end, said annular open end aligned with and sealed to one open end of said cuff, wherein a combination of said cuff and said sleeve define a condom.

2. A device as in claim 1, further comprising at least one elastic ring coupled to said at least one wall region.

3. A device as in claim 2, wherein said at least one elastic ring includes a first ring having a radial width in the range of approximately 0.1875 inches to approximately 0.5 inches and an axial length in the range of approximately 0.1875 inches to approximately 5 inches.

4. A device as in claim 1, wherein said void region has a width dimension in the range of approximately 0.125 inches to approximately 0.75 inches.

5. A device as in claim 2, wherein said at least one elastic ring includes a first ring and a second ring, said first ring coupled to a first longitudinal end of said at least one wall region and said second ring coupled to said at least one wall region and spaced apart from said first ring.

6. A device as in claim 5, wherein said second ring is coupled to a second longitudinal end of said at least one wall region.

7. A device as in claim 1, further comprising indicia on said at least one wall region, said indicia being located in diametric opposition to said void region.

8. A device as in claim 1, wherein said at least one wall region comprises a hollow and open-ended cylinder having a longitudinal slit defining said void region.

9. A device as in claim 1, wherein said at least one wall region comprises an open-ended cylinder having an interior surface, and further comprising a pair of ridges coupled to and extending axially along said interior surface to define said void region.

10. A device as in claim 1, wherein said at least one wall region has a thickness dimension of approximately 0.1 inches to approximately 0.5 inches.

11. A device as in claim 1, wherein said at least one wall region comprises a plurality of spaced apart wall regions.

12. A device as in claim 1, wherein opposing longitudinal ends of said at least one wall region are tapered.

13. A device as in claim 1, further comprising a flaccid material coupled to said at least one wall region and spanning said void region.

14. A device as in claim 3, further comprising a notch defined in said first ring, said notch facing radially inward of said first ring and extending along said axial length thereof.

15. A device as in claim 14, wherein a base of said notch has a span in the range of approximately 0.125 inches to approximately 0.75 inches.

16. A device providing erection assistance, comprising an open-ended tubular cuff adapted to fit over a male penis and having a length extending from the base of the penis to as far as the corona of the penis, said cuff including
  at least one wall region defining a void region along said length;
  a first elastic ring coupled to said at least one wall region;
  a second elastic ring coupled to said at least one wall region and spaced apart from said first elastic ring; and
  indicia on said at least one wall region, said indicia being located in diametric opposition to said void region.

17. A device as in claim 16, wherein said first elastic ring includes a first ring having a radial width in the range of approximately 0.1875 inches to approximately 0.5 inches and an axial length in the range of approximately 0.1875 inches to approximately 5 inches.

18. A device as in claim 16, wherein said void region has a width dimension in the range of approximately 0.125 inches to approximately 0.75 inches.

19. A device as in claim 16, wherein said first elastic ring is coupled to a first longitudinal end of said at least one wall region and said second elastic ring is coupled to a second longitudinal end of said at least one wall region.

20. A device as in claim 16, wherein said at least one wall region comprises a hollow and open-ended cylinder having a longitudinal slit defining said void region.

21. A device as in claim 16, wherein said at least one wall region comprises an open-ended cylinder having an interior surface, and further comprising a pair of ridges coupled to and extending axially along said interior surface to define said void region.

22. A device as in claim 16, wherein said at least one wall region has a thickness dimension of approximately 0.1 inches to approximately 0.5 inches.

23. A device as in claim 16, wherein said at least one wall region comprises a plurality of spaced apart wall regions.

24. A device as in claim 16, wherein opposing longitudinal ends of said at least one wall region are tapered.

25. A device as in claim 16, further comprising a flaccid material coupled to said at least one wall region and spanning said void region.

26. A device as in claim 16, wherein said first elastic ring is coupled to a first longitudinal end of said at least one wall region, said device further comprising a sleeve of flaccid and elastic material having an annular open end and a closed end, said annular open end being aligned with and sealed to said first elastic ring.

27. A device as in claim 17, further comprising a notch defined in said first elastic ring, said notch facing radially inward of said first elastic ring and extending along said axial length thereof.

28. A device as in claim 27, wherein a base of said notch has a span in the range of approximately 0.125 inches to approximately 0.75 inches.

29. A device providing erection assistance, comprising an open-ended tubular cuff adapted to fit over a male penis and having a length extending from the base of the penis to as far as the corona of the penis, said cuff including
  at least one wall region having a first longitudinal end and a second longitudinal end, said at least one wall region defining a void region between said first longitudinal end and said second longitudinal end, said at least one wall region having a thickness dimension of approximately 0.1 inches to approximately 0.5 inches;
  a first elastic ring coupled to said first longitudinal end; and
  a second elastic ring coupled to said second longitudinal end.

30. A device as in claim 29, wherein said first elastic ring has a radial width in the range of approximately 0.1875 inches to approximately 0.5 inches and an axial length in the range of approximately 0.1875 inches to approximately 5 inches.

31. A device as in claim 29, wherein said void region has a width dimension in the range of approximately 0.125 inches to approximately 0.75 inches.

32. A device as in claim 29, further comprising indicia on said at least one wall region, said indicia being located in diametric opposition to said void region.

33. A device as in claim 29, wherein said at least one wall region comprises a hollow and open-ended cylinder having a longitudinal slit defining said void region.

34. A device as in claim 29, wherein said at least one wall region comprises a plurality of spaced apart wall regions.

35. A device as in claim 29, further comprising a flaccid material coupled to said at least one wall region and spanning said void region.

36. A device as in claim 29, further comprising a sleeve of flaccid and elastic material having an annular open end and a closed end, said annular open end being aligned with and sealed to said first elastic ring.

37. A device as in claim 36, further comprising indicia on at least one of said sleeve and said at least one wall region, said indicia being located in diametric opposition to said void region.

38. A device as in claim 30, further comprising a notch defined in said first elastic ring, said notch facing radially inward of said first elastic ring and extending along said axial length thereof.

39. A device as in claim 38, wherein a base of said notch has a span in the range of approximately 0.125 inches to approximately 0.75 inches.

\* \* \* \* \*